(12) United States Patent
Hildebrand et al.

(10) Patent No.: US 7,364,901 B2
(45) Date of Patent: Apr. 29, 2008

(54) RECOMBINANT STOKESIA EPOXYGENASE GENE

(75) Inventors: David Hildebrand, Lexington, KY (US); Tomoko Hatanaka, Hyogo (JP)

(73) Assignee: University of Kentucky Research Foundation, Lexington, KY (US)

( * ) Notice: Subject to any disclaimer, the term of this patent is extended or adjusted under 35 U.S.C. 154(b) by 328 days.

(21) Appl. No.: 10/622,774

(22) Filed: Jul. 21, 2003

(65) Prior Publication Data
US 2005/0022270 A1     Jan. 27, 2005

Related U.S. Application Data

(60) Provisional application No. 60/396,406, filed on Jul. 19, 2002.

(51) Int. Cl.
C12N 5/14    (2006.01)
C12N 15/63   (2006.01)
C12N 1/21    (2006.01)
C12N 1/15    (2006.01)
C07H 21/02   (2006.01)

(52) U.S. Cl. .............. 435/419; 435/320.1; 435/252.3; 435/254.11; 536/23.1; 536/23.6

(58) Field of Classification Search ............... None
See application file for complete search history.

(56) References Cited

U.S. PATENT DOCUMENTS

| | | | |
|---|---|---|---|
| 4,459,355 A | 7/1984 | Cello et al. | |
| 4,536,475 A | 8/1985 | Anderson | |
| 4,945,050 A | 7/1990 | Sanford et al. | |
| 5,036,006 A | 7/1991 | Sanford et al. | |
| 5,100,792 A | 3/1992 | Sanford et al. | |
| 5,177,010 A | 1/1993 | Goldman et al. | |
| 5,179,022 A | 1/1993 | Sanford et al. | |
| 5,204,253 A | 4/1993 | Sanford et al. | |
| 5,371,014 A | 12/1994 | Matsuyama et al. | |
| 5,405,765 A | 4/1995 | Vasil et al. | |
| 5,464,763 A | 11/1995 | Schilperoort et al. | |
| 5,478,744 A | 12/1995 | Sanford et al. | |
| 5,484,956 A | 1/1996 | Lundquist et al. | |
| 5,489,520 A | 2/1996 | Adams et al. | |
| 5,508,468 A | 4/1996 | Lundquist et al. | |
| 5,510,318 A | 4/1996 | Patel et al. | |
| 5,538,877 A | 7/1996 | Lundquist et al. | |
| 5,554,798 A | 9/1996 | Lundquist et al. | |
| 5,565,346 A | 10/1996 | Facciotti | |
| 5,846,784 A * | 12/1998 | Hitz .................... | 435/91.2 |
| 6,329,518 B1 | 12/2001 | Green et al. | |

FOREIGN PATENT DOCUMENTS

| EP | 0 442 174 A1 | 8/1991 |
|---|---|---|
| EP | 0 486 233 B1 | 5/1992 |
| EP | 0 486 234 B1 | 5/1992 |
| EP | 0 604 662 A1 | 7/1994 |
| EP | 0 672 752 A1 | 9/1995 |
| EP | 0 674 725 B1 | 10/1995 |
| EP | 0 539 563 B1 | 10/2001 |
| WO | WO 91/02071 | 2/1991 |
| WO | WO 94/11516 | 5/1994 |
| WO | WO 95/06128 | 3/1995 |
| WO | WO 98/46762 | 10/1998 |
| WO | WO 98/56922 | 12/1998 |
| WO | WO 02/08269 A2 | 1/2002 |

OTHER PUBLICATIONS

Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Clough, Steven J., et al. "Floral Dip: a simplified method for Agrobacterium-mediated transformation of *Arabidopsis thaliana*," Blackwell Science Ltd., 1999, The Plant Journal (1988) 16(6), pp. 735-743.
Lee, Michael., et al. "Identification of Non-Heme Diiron Proteins That Catalyze Triple Bond and Epoxy Group Formation." Science, vol. 280, May 8, 1998, pp. 915-918.
Broun, Pierre., et al " Accumultaion of Ricinoleic, Lesquerolic, and Densipolic Acids In Seeds of Transgenic Arabldopsis Plants That Express a Fatty Acyl Hydroxylase cDNA from Castor Bean." Plant Physiol. (1997), 113, pp. 933-942.
Cahoon, Edgar B. Transgenic Production of Epoxy Fatty Acids by Expression of a Cytochrome P450 Enzyme from *Euphorbia lagascae* Seed. Plant Physiology, Feb. 2002, vol. 128, pp. 615-624.
Bafor, Maureen., et al. "Biosynthesis of Vernoleate (cis-12-Epoxyoctadeca-cis-9-enoate) in Microsomal Preparations from Developing Endosperm of *Euphoribia lagascae*." Archives of Biochemistry and Biophysics, vol. 303, No. 1, May 15, pp. 145-151, 1993.
Hildebrand, David., et al. "Redirecting Lipid Metabolism In Plants." Department of Agronomy, university of Kentucky, Lexington Kentucky, 40546-0091, pp. 1-68.
Seither, Craig Anthony, Thesis: Characterization of Epoxy Fatty Acid Synthesis In *Vernonia galamensis* and the Isolation of Candidate cDNA Clones. pp. 1-107.

* cited by examiner

*Primary Examiner*—Phuong T. Bui
*Assistant Examiner*—Vinod Kumar
(74) *Attorney, Agent, or Firm*—McDermott Will & Emery LLP (57) ABSTRACT

A chimeric gene comprising an isolated nucleic acid molecule encoding a delta 12-fatty acid epoxygenase enzyme and transgenic plants containing the chimeric gene are described. Expression of the chimeric delta 12-epoxygenase gene leads to altered levels of fatty acids in transformed cells.

10 Claims, 7 Drawing Sheets

|          | 1                                                    50 |
|----------|----------|----------|----------|----------|----------|
| Stokesia | ~~~~~~~~~~ | ~~~~~~~~~ | GTAGGTTTTG | GGTGTCGGTG | AGATCAGTGT |
| Vernonia | TTATGAAAGC | TCGATCGGTG | TTCGATCAAT | TCAAATCGAC | GAACACGAAA |
| Crepis   | ~~~~~~~~~ | ~~~~~~~~~ | ~~~~~~~~~ | ~~~~~~~~~ | ~~~~~~~~~ |

|          | 51                                                   100 |
|----------|----------|----------|----------|----------|----------|
| Stokesia | TCGACCGAAA | TCCAACGCAT | TTTCTAATTT | GGATTTCAGA | AATCTGGGAG |
| Vernonia | TCGAACTCAA | CAATTCAAAT | CTGGAAATAT | TAATTGGATC | AAGCGGGCGG |
| Crepis   | ~~~~~~~~~ | ~~~~~~~~~ | ~~~~~~~~~ | ~~~~~~~~~ | ~~~~gagaag |

|          | 101                                                  150 |
|----------|----------|----------|----------|----------|----------|
| Stokesia | AAGGTAGCAG | AATGTCGGAT | TCATATGATG | ATC....... | .....GAATG |
| Vernonia | A...TATGAT | GATGTCGGAT | TCATGTGATG | ATCATGATCA | GCTGGTGAAA |
| Crepis   | ttgaccataa | atcatttatc | aacatgggtg | ccggcggtcg | tggtcggaca |

|          | 151                                                  200 |
|----------|----------|----------|----------|----------|----------|
| Stokesia | AAAGATCATG | ATATGGACGA | ACGAGCCCCG | ATTGATCCGG | CGCCATTCTC |
| Vernonia | GATGATCATA | ATATAAACGA | ACGTGCACCG | GTTGATGCGG | CACCATTCTC |
| Crepis   | tcggaaaaat | cggtcatgga | acgtgtctca | gttgatccag | taaccttctc |

|          | 201                                                  250 |
|----------|----------|----------|----------|----------|----------|
| Stokesia | GTTAAGTGAT | CTAAAGAAAG | CAATCCCTGC | ACATTGCTTC | CGGCGATCCG |
| Vernonia | GTTAAGCGAT | CTAAAGAAAG | CAATCCCTCC | GCATTGCTTC | CAGCGATCTG |
| Crepis   | actgagtgaa | ttgaagcaag | caatccctcc | ccattgcttc | cagagatctg |

|          | 251                                                  300 |
|----------|----------|----------|----------|----------|----------|
| Stokesia | CCGTCTGGTC | ATCCTGCTAC | GTAGTTCAGG | ATCTCATTAT | CACCTTCCTT |
| Vernonia | CCATCCGTTC | ATCGTGCTAC | GTTGTTCAGG | ATCTCATTAT | TACCTTCCTT |
| Crepis   | taatccgctc | atcttactat | gttgttcaag | atctcattat | tgcctacatc |

|          | 301                                                  350 |
|----------|----------|----------|----------|----------|----------|
| Stokesia | TTATACACGG | TCGCCAACAC | CTACATTCCT | CACCTCCCTC | CTCCTCTAGT |
| Vernonia | TTATACACGC | TCGCCAACTC | TTACATTCCT | CTTCTTCCTC | CTCCTCTACC |
| Crepis   | ttctacttcc | ttgccaacac | atatatccct | actcttccta | ctagtctagc |

|          | 351                                                  400 |
|----------|----------|----------|----------|----------|----------|
| Stokesia | TTACTTAGCA | TGGCCGGTTT | ACTGGTTTTG | CCAATCTTGC | ATCCTCACTG |
| Vernonia | TTACTTAGCA | TGGCCTGTTT | ACTGGTTTTG | CCAATCTTCG | ATCCTCACTG |
| Crepis   | ctacttagct | tggcccgttt | actggttctg | tcaagctagc | gtcctcactg |

|          | 401                                                  450 |
|----------|----------|----------|----------|----------|----------|
| Stokesia | GTTTATGGGT | CCTCGGCCAT | GAATGCGGCC | ATCATGCCTT | TAGTGAGTAC |
| Vernonia | GTTTATGGGT | CATTGGCCAT | GAATGTGGCC | ATCATGCTTA | TAGTGAGTAC |
| Crepis   | gcttatggat | cctcggccac | gaatgtggtc | accatgcctt | tagcaactac |

|          | 451                                                  500 |
|----------|----------|----------|----------|----------|----------|
| Stokesia | CAGTGGATTG | ATAACGCCGT | TGGATTCGTC | CTCCATTCGG | CTCTCCTCAC |
| Vernonia | CAGTGGGTTG | ATAACACCGT | TGGATTCATC | CTCCATTCCT | TTCTTCTCAC |
| Crepis   | acatggtttg | acgacactgt | gggcttcatc | ctccactcat | ttctcctcac |

|          | 501                                                  550 |
|----------|----------|----------|----------|----------|----------|
| Stokesia | CCCTTACTTT | TCTTGGAAAT | ACAGCCATCG | AAAGCACCAT | GCAAACACAA |
| Vernonia | ACCTTACTTT | TCTTGGAAAT | ACAGCCATCG | AAAGCACCAT | GCCAACACGA |

Figure 1A

|  |  |  |  |  |  |
|---|---|---|---|---|---|
| Crepis |  | cccgtatttc | tcttggaaat | tcagtcaccg | gaatcaccat | tccaacacaa |
| Stokesia | 551<br>ATTCACTCGA | AAACGAGGAA | GTTTACATTC | CTAGAACTCA | 600<br>GTCCCAGCTC |
| Vernonia | ATTCACTCGA | AAACGAGGAG | GTTTACATTC | CTAAAGCCAA | GTCCCAGCTC |
| Crepis | gttcgattga | taacgatgaa | gtttacattc | cgaaaagcaa | gtccaaactc |
| Stokesia | 601<br>AGGACTTACT | CCACATACGA | ATTTCTTGAC | AACACGCCTG | 650<br>GTCGAATCCT |
| Vernonia | AGGAATTACT | CCAATTTCAA | ATTTCTTGAC | AACACCCCTG | GTCGAATCTT |
| Crepis | gcgcgt.... | ..atctataa | acttcttaac | aacccacctg | gtcggctgtt |
| Stokesia | 651<br>CATCTTGGTC | ATCATGTTAA | CCTTAGGATT | TCCTTTATAC | 700<br>CTCTTAACGA |
| Vernonia | CATTTTGCTT | ATCATGTTGA | CCTTGGGCTT | TCCTTTATAC | CTCTTGACCA |
| Crepis | ggttttgatt | atcatgttca | ccctaggatt | tcctttatac | ctcttgacaa |
| Stokesia | 701<br>ATGTTTCAGG | CAAGAAGTAC | GATAGATTTA | CCAACCACTT | 750<br>TGATCCATTG |
| Vernonia | ATATTTCAGG | CAAGAAATAC | CAAAGGTTTG | CCAACCACTT | TGATCCGTTG |
| Crepis | atatttccgg | caagaaatac | gacaggtttg | ccaaccactt | cgacccatg |
| Stokesia | 751<br>AGCCCGATCT | TCACCGAGCG | TGAGCGAATC | CAGGTTGCGT | 800<br>TATCAGATCT |
| Vernonia | AGCCCCATCT | TCAGTGAGCG | TGAACGAATC | CAGGTCGTGC | TATCGGATGT |
| Crepis | agtccaattt | tcaaagaacg | tgagcggttt | caggtcttcc | tttcggatct |
| Stokesia | 801<br>TGGTATCGTT | GCAGTGTTTT | ACGGACTCAA | GTTCTTGTA | 850<br>CAAACAAAAG |
| Vernonia | GGGTCTCATT | GCTGTGTTTT | ACGGGCTTAA | GTTCTTGTA | GCGAAAAAG |
| Crepis | tggtcttctt | gccgtgtttt | atggaattaa | agttgctgta | gcaaataaag |
| Stokesia | 851<br>GATTTGGTTG | GGTGATGTGC | ATGTATGGAG | TTCCAGTGAT | 900<br>AGGTCTGAAT |
| Vernonia | GGTTCGGTTG | GGTAATGCGC | ATGTACGGAG | CCCCAGTGGT | TGGGCTGAAT |
| Crepis | gagctgcttg | ggtagcgtgc | atgtatggag | ttccggtatt | aggcgtattt |
| Stokesia | 901<br>TCCTTCATTA | TCGTAATCAC | TTATCTGCAC | CACACACATC | 950<br>TGTCGTCACC |
| Vernonia | GCCTTCATAA | TAATGATCAC | TTATCTCCAC | CACACCCATC | TGTCTTCGCC |
| Crepis | acctttttcg | atgtgatcac | cttcttgcac | cacacccatc | agtcgtcgcc |
| Stokesia | 951<br>CCATTACGAT | TCAACCGAAT | GGAACTGGAT | CAAAGGAGCC | 1000<br>TTGACCACAA |
| Vernonia | TCATTACGAT | TCGACCGAAT | GGAACTGGAT | CAAAGGAGCC | TTGACTACAA |
| Crepis | tcattatgat | tcaactgaat | ggaactggat | cagagggcc | ttgtcagcaa |
| Stokesia | 1001<br>TCGACAGAGA | TTTCGGTCTC | CTGAATCGGG | TTTTCCACGA | 1050<br>CGTTACACAC |
| Vernonia | TCGATAGAGA | TTTCGGTCTC | CTGAATAGGG | TGTTCCATGA | CGTCACTCAC |
| Crepis | tcgataggga | ctttggattc | ctgaatagtg | ttttccatga | tgttacacac |
| Stokesia | 1051<br>ACCCACGTGT | TGCACCATTT | GTTTCCCTAC | ATTCCACATT | 1100<br>ATCATGCAAA |
| Vernonia | ACACACGTGT | TGCATCATTT | GTTCCCGTAC | ATTCCACATT | ATCATGCAAA |

Figure 1B

```
Crepis      actcatgtca tgcatcattt gttttcatac attccacact atcatgcaaa 1101                                                1150
Stokesia    GGAGGCAAGC GAGGCCATCA AGCCAATCTT GGGTGATTAC AGGATGATCG
Vernonia    GGAGGCGAGC GACGCAATAA AGCCGGTGTT AGGGGAGTAT CGGATGATCG
Crepis      ggaggcaagg gatgcaatca agccaatctt gggcgacttt tatatgatcg 1151                                                1200
Stokesia    ACAGGACTCC ATTTTTCAAA GCAATGTGGA GAGAGGCCAA GGAATGCATT
Vernonia    ATAGGACTCC GTTTTACAAA GCAATGTGGA GAGAGGCGAA GGAATGCATC
Crepis      acaggactcc aattttaaaa gcaatgtgga gagagggcag ggagtgcatg 1201                                                1250
Stokesia    TACATCGAGC AAGATGCAGA CAGCAAGCAC AAAGGGACAT ATTGGTACCA
Vernonia    TACATCGAGC CAGATGAAGA TAAGAAGCAC AAAGGTGTAT ATTGGTACCA
Crepis      tacatcgagc ctgat..... .agcaagctc aaaggtgttt attggtatca 1251                                                1300
Stokesia    TAAAATGTAA TCGATGATGG AGTTTAGTTG GAAATAATGA CATGCAGCAT
Vernonia    TAAAATGTGA TACGAGCTGA GTACGTAGTA CGTTGTATGC TTTTGTAACG
Crepis      taaattgtga tcatatgcaa aatgcacatg cattttcaaa ccctctagtt 1301                                                1350
Stokesia    CCCTTTTGTA TGCTTGAATC GTTCTATTTC TTTATATGTT TTGTAAGATA
Vernonia    TTTTGTAAGA TAAATAAATA AATCTTGAAT GAAGATAAAA AAAAAAAAAA
Crepis      acgtttgttc tatgtataat aaaccgccgg tcctttggtt gactatgcct 1351                                                1400
Stokesia    AATAAGTAAA TCTTTGAGTG AAGATGGGGA GCAGGAAACA AGCAGAATAT
Vernonia    AAAAAAAAAA.AAAAAAA~~~ ~~~~~~~~~~ ~~~~~~~~~~ ~~~~~~~~~~
Crepis      aagccaggcg aaacagttaa ataatatcgg tatgatgtgt aatgaaagta 1401                                                1450
Stokesia    AATACGCTAA AAAAAAAAAA AAAAAAAAAA AAAAAAAA~~ ~~~~~~~~~~
Vernonia    ~~~~~~~~~~ ~~~~~~~~~~ ~~~~~~~~~~ ~~~~~~~~~~ ~~~~~~~~~~
Crepis      tgtggttgtc tggttttgtt gctatgaaag aaagtatgtg gttgtcggtc
```

Figure 3B

SEQUENCE LISTING

<160> NUMBER OF SEQ ID NOS: 10

<210> SEQ ID NO 1
<211> LENGTH: 1406
<212> TYPE: DNA
<213> ORGANISM: Stokesia laevis

<400> SEQUENCE: 1

```
gtaggttttg ggtgtcggtg agatcagtgt tcgaccgaaa tccaacgcat tttctaattt      60
ggatttcaga aatctgggag aaggtagcag aatgtcggat tcatatgatg atcgaatgaa     120
agatcatgat atggacgaac gagccccgat tgatccggcg ccattctcgt taagtgatct     180
aaagaaagca atccctgcac attgcttccg gcgatccgcc gtctggtcat cctgctacgt     240
agttcaggat ctcattatca ccttcctttt atacacggtc gccaacacct acattcctca     300
cctccctcct cctctagttt acttagcatg gccggtttac tggttttgcc aatcttgcat     360
cctcactggt ttatgggtcc tcggccatga atgcggccat catgccttta gtgagtacca     420
gtggattgat aacgccgttg gattcgtcct ccattcggct ctcctcaccc cttacttttc     480
ttggaaatac agccatcgaa agcaccatgc aaacacaaat tcactcgaaa acgaggaagt     540
ttacattcct agaactcagt cccagctcag gacttactcc acatacgaat ttcttgacaa     600
cacgcctggt cgaatcctca tcttggtcat catgttaacc ttaggatttc ctttatacct     660
cttaacgaat gtttcaggca agaagtacga tagatttacc aaccactttg atccattgag     720
cccgatcttc accgagcgtg agcgaatcca ggttcgtta tcagatcttg gtatcgttgc     780
agtgttttac ggactcaagt ttcttgtaca aacaaaagga tttggttggg tgatgtgcat     840
gtatggagtt ccagtgatag gtctgaattc cttcattatc gtaatcactt atctgcacca     900
cacacatctg tcgtcacccc attacgattc aaccgaatgg aactggatca aaggagcctt     960
```

```
gaccacaatc gacagagatt tcggtctcct gaatcgggtt ttccacgacg ttacacacac    1020
ccacgtgttg caccatttgt ttccctacat tccacattat catgcaaagg aggcaagcga    1080
ggccatcaag ccaatcttgg gtgattacag gatgatcgac aggactccat ttttcaaagc    1140
aatgtggaga gaggccaagg aatgcattta catcgagcaa gatgcagaca gcaagcacaa    1200
agggacatat tggtaccata aaatgtaatc gatgatggag tttagttgga ataatgaca     1260 tgcagcatcc cttttgtatg cttgaatcgt tctatttctt tatatgtttt gtaagataaa    1320
taagtaaatc tttgagtgaa gatggggagc aggaaacaag cagaatataa tacgctaaaa    1380
aaaaaaaaaa aaaaaaaaaa aaaaaa                                         1406
```

<210> SEQ ID NO 2
<211> LENGTH: 378
<212> TYPE: PRT
<213> ORGANISM: Stokesia laevis

<400> SEQUENCE: 2

```
Met Ser Asp Ser Tyr Asp Asp Arg Met Lys Asp His Asp Met Asp Glu
1               5                   10                  15

Arg Ala Pro Ile Asp Pro Ala Pro Phe Ser Leu Ser Asp Leu Lys Lys
                20                  25                  30

Ala Ile Pro Ala His Cys Phe Arg Arg Ser Ala Val Trp Ser Ser Cys
            35                  40                  45

Tyr Val Val Gln Asp Leu Ile Ile Thr Phe Leu Leu Tyr Thr Val Ala
        50                  55                  60

Asn Thr Tyr Ile Pro His Leu Pro Pro Pro Leu Val Tyr Leu Ala Trp
65                  70                  75                  80

Pro Val Tyr Trp Phe Cys Gln Ser Cys Ile Leu Thr Gly Leu Trp Val
                85                  90                  95

Leu Gly His Glu Cys Gly His His Ala Phe Ser Glu Tyr Gln Trp Ile
            100                 105                 110

Asp Asn Ala Val Gly Phe Val Leu His Ser Ala Leu Leu Thr Pro Tyr
        115                 120                 125

Phe Ser Trp Lys Tyr Ser His Arg Lys His His Ala Asn Thr Asn Ser
    130                 135                 140

Leu Glu Asn Glu Glu Val Tyr Ile Pro Arg Thr Gln Ser Gln Leu Arg
145                 150                 155                 160

Thr Tyr Ser Thr Tyr Glu Phe Leu Asp Asn Thr Pro Gly Arg Ile Leu
                165                 170                 175

Ile Leu Val Ile Met Leu Thr Leu Gly Phe Pro Leu Tyr Leu Leu Thr
            180                 185                 190

Asn Val Ser Gly Lys Lys Tyr Asp Arg Phe Thr Asn His Phe Asp Pro
        195                 200                 205

Leu Ser Pro Ile Phe Thr Glu Arg Glu Arg Ile Gln Val Ala Leu Ser
    210                 215                 220

Asp Leu Gly Ile Val Ala Val Phe Tyr Gly Leu Lys Phe Leu Val Gln
225                 230                 235                 240

Thr Lys Gly Phe Gly Trp Val Met Cys Met Tyr Gly Val Pro Val Ile
                245                 250                 255

Gly Leu Asn Ser Phe Ile Ile Val Ile Thr Tyr Leu His His Thr His
            260                 265                 270

Leu Ser Ser Pro His Tyr Asp Ser Thr Glu Trp Asn Trp Ile Lys Gly
        275                 280                 285

Ala Leu Thr Thr Ile Asp Arg Asp Phe Gly Leu Leu Asn Arg Val Phe
```

```
                  290                 295                 300
His Asp Val Thr His Thr His Val Leu His His Leu Phe Pro Tyr Ile
305                 310                 315                 320

Pro His Tyr His Ala Lys Glu Ala Ser Glu Ala Ile Lys Pro Ile Leu
                325                 330                 335

Gly Asp Tyr Arg Met Ile Asp Arg Thr Pro Phe Phe Lys Ala Met Trp
                340                 345                 350

Arg Glu Ala Lys Glu Cys Ile Tyr Ile Glu Gln Asp Ala Asp Ser Lys
            355                 360                 365

His Lys Gly Thr Tyr Trp Tyr His Lys Met
        370                 375

<210> SEQ ID NO 3
<211> LENGTH: 8
<212> TYPE: PRT
<213> ORGANISM: Crepis palaestina and Vernonia galamensis

<400> SEQUENCE: 3

Cys His Glu Cys Gly His His Ala
1               5

<210> SEQ ID NO 4
<211> LENGTH: 8
<212> TYPE: PRT
<213> ORGANISM: Crepis palaestina and Vernonia galamensis

<400> SEQUENCE: 4

His Asp Val Thr His Thr His Val
1               5

<210> SEQ ID NO 5
<211> LENGTH: 26
<212> TYPE: DNA
<213> ORGANISM: Stokesia laevis

<400> SEQUENCE: 5
cgcaacctgg attcgctcac gctcgg                                        26

<210> SEQ ID NO 6
<211> LENGTH: 27
<212> TYPE: DNA
<213> ORGANISM: Stokesia laevis

<400> SEQUENCE: 6
cccagctcag gacttactcc acatacg                                       27

<210> SEQ ID NO 7
<211> LENGTH: 32
<212> TYPE: DNA
<213> ORGANISM: Artificial Sequence
<220> FEATURE:
<223> OTHER INFORMATION: Artificial StexpF primer of unknown origin

<400> SEQUENCE: 7
gacgcgtctt cccatgtcgg attcatatga tg                                 32

<210> SEQ ID NO 8
<211> LENGTH: 37
<212> TYPE: DNA
<213> ORGANISM: Artificial Sequence
<220> FEATURE:
<223> OTHER INFORMATION: Artificial StexpR primer of unknown origin
```

-continued

```
<400> SEQUENCE: 8
gacgcccggg ttacatttta tggtaccaat atgtccc                              37

<210> SEQ ID NO 9
<211> LENGTH: 1364
<212> TYPE: DNA
<213> ORGANISM: Veronia galamensis

<400> SEQUENCE: 9
ttatgaaagc tcgatcggtg ttcgatcaat tcaaatcgac gaacacgaaa tcgaactcaa     60
caattcaaat ctggaaatat taattggatc aagcgggcgg atatgatgat gtcggattca    120
tgtgatgatc atgatcagct ggtgaaagat gatcataata taaacgaacg tgcaccggtt    180
gatgcggcac cattctcgtt aagcgatcta agaaaagcaa tccctccgca ttgcttccag    240
cgatctgcca tccgttcatc gtgctacgtt gttcaggatc tcattattac cttccttta    300 tacacgctcg ccaactctta cattcctctt cttcctcctc ctctacctta cttagcatgg    360
cctgtttact ggttttgcca atcttcgatc ctcactggtt tatgggtcat ggccatgaa     420 tgtggccatc atgcttatag tgagtaccag tgggttgata cacccgttgg attcatcctc    480
cattcctttc ttctcacacc ttactttttct tggaaataca gccatcgaaa gcaccatgcc   540
aacacgaatt cactcgaaaa cgaggaggtt tacattccta agccaagtc ccagctcagg     600 aattactcca atttcaaatt tcttgacaac acccctggtc gaatcttcat tttgcttatc    660
atgttgacct tgggctttcc tttataccte ttgaccaata tttcaggcaa gaaataccaa    720
aggtttgcca accactttga tccgttgagc cccatcttca gtgagcgtga acgaatccag    780
gtcgtgctat cggatgtggg tctcattgct gtgttttacg gcttaagtt tcttgtagcg     840 aaaaaagggt tcggttgggt aatgcgcatg tacggagccc cagtggttgg gctgaatgcc    900
ttcataataa tgatcactta tctccaccac acccatctgt cttcgcctca ttacgattcg    960
accgaatgga actggatcaa aggagccttg actacaatcg atagagattt cggtctcctg   1020
aatagggtgt tccatgacgt cactcacaca cacgtgttgc atcatttgtt cccgtacatt   1080
ccacattatc atgcaaagga ggcgagcgac gcaataaagc cggtgttagg ggagtatcgg   1140
atgatcgata ggactccgtt ttacaaagca atgtggagag aggcgaagga atgcatctac   1200
atcgagccag atgaagataa gaagcacaaa ggtgtatatt ggtaccataa aatgtgatac   1260
gagctgagta cgtagtacgt tgtatgcttt tgtaacgttt tgtaagataa ataaataaat   1320
cttgaatgaa gataaaaaaa aaaaaaaaa aaaaaaaaaa aaaa                     1364

<210> SEQ ID NO 10
<211> LENGTH: 1344
<212> TYPE: DNA
<213> ORGANISM: Crepis palaestina

<400> SEQUENCE: 10
gagaagttga ccataaatca tttatcaaca tgggtgccgg cggtcgtggt cggacatcgg     60
aaaaatcggt catggaacgt gtctcagttg atccagtaac cttctcactg agtgaattga   120
agcaagcaat ccctcccat tgcttccaga gatctgtaat ccgctcatct tactatgttg    180
ttcaagatct cattattgcc tacatcttct acttccttgc caacacatat atccctactc   240
ttcctactag tctagcctac ttagcttggc ccgtttactg gttctgtcaa gctagcgtcc    300
tcactggctt atggatcctc ggccacgaat gtggtcacca tgcctttagc aactacacat   360
ggtttgacga cactgtgggc ttcatcctcc actcatttct cctcaccccg tatttctctt   420
```

```
                                            -continued
ggaaattcag tcaccggaat caccattcca acacaagttc gattgataac gatgaagttt      480
acattccgaa aagcaagtcc aaactcgcgc gtatctataa acttcttaac aacccacctg      540
gtcggctgtt ggttttgatt atcatgttca ccctaggatt tcctttatac ctcttgacaa      600
atatttccgg caagaaatac gacaggtttg ccaaccactt cgaccccatg agtccaattt      660
tcaaagaacg tgagcggttt caggtcttcc tttcggatct tggtcttctt gccgtgtttt      720
atggaattaa agttgctgta gcaaataaag gagctgcttg ggtagcgtgc atgtatggag      780
ttccggtatt aggcgtattt accttttcg atgtgatcac cttcttgcac cacacccatc       840
agtcgtcgcc tcattatgat tcaactgaat ggaactggat cagaggggcc ttgtcagcaa      900
tcgatagaga ctttggattc ctgaatagtg ttttccatga tgttacacac actcatgtca      960
tgcatcattt gttttcatac attccacact atcatgcaaa ggaggcaagg gatgcaatca     1020
agccaatctt gggcgacttt tatatgatcg acaggactcc aattttaaaa gcaatgtgga     1080
gagagggcag ggagtgcatg tacatcgagc ctgatagcaa gctcaaaggt gtttattggt     1140
atcataaatt gtgatcatat gcaaaatgca catgcatttt caaaccctct agttacgttt     1200
gttctatgta taataaaccg ccggtccttt ggttgactat gcctaagcca ggcgaaacag     1260
ttaaataata tcggtatgat gtgtaatgaa agtatgtggt tgtctggttt tgttgctatg     1320
aaagaaagta tgtggttgtc ggtc                                            1344
```

RECOMBINANT STOKESIA EPOXYGENASE GENE

RELATED APPLICATIONS

This application claims the benefit of provisional application 60/396,406, filed Jul. 19, 2002, which is incorporated herein in its entirety

FIELD OF THE INVENTION

The present invention relates to a novel nucleic acid molecule encoding an enzyme involved in fatty acid biosynthesis and modification in plants and seeds. This nucleic acid molecule preferably originates from *Stokesia laevis*. The invention extends to genetically improved cost-effective raw materials for use in the efficient production of a variety of industrial products including coating, composites, adhesives and plasticizers.

BACKGROUND OF THE INVENTION

Epoxy fatty acids contain oxygen bridges across adjacent carbon atoms at a single or multiples positions in the acyl chain, making them highly reactive and prone to cross-linking. These properties make epoxy fatty acids valuable raw materials, particularly for epoxy coating and plasticizers. Currently, epoxidized soybean and linseed oils are produced by introducing an epoxy group across the double bond of polyunsaturated fatty acids. This is a costly process and it would likely be more economical if the biosynthetic reactions in oilseed themselves converted the polyunsaturated fatty acids into epoxy fatty acids. However, there currently is no known way to produce a commercial oilseed that accumulates epoxy fatty acids by conventional breeding and genetics.

Certain genotypes of several plant species accumulate high level of epoxy fatty acids in the seed oil. Epoxy fatty acids, like vernolic (E-12,13-epoxyoctadeca-E-9-enoic) and coronaric (E-9,10-epoxyoctadeca-E-12-enoic) acids, have been found as a component of the seed oil of species represented by a number of plant families such as Asteraceae, Euphorbiceae, pnagraceae, and Valerianaceae (Smith, 1970). One of the highest known accumulators of vernolic acid is *Vernonia galamensis* in which vernolic acid constitues 80% of triglyceride fatty acids (Perdue, 1989; Pascal and Correal, 1992; Thompson et al., 1994). *Stokesia laevis* is in the Asteraceae family, and the seed soil is also made up of about 60-70% vernolic acid (Gunstone, 1993).

Many plants are known to possess enzymes that transform unsaturated fatty acids into epoxy fatty acids (Gardner, 1991; Gardner et al., 1991; Blee, 1998). The process by which the seeds of certain species of *Vernonia*, *Stokesia* and *Euphorbia* appears to be due to an enzyme not present in major commercial oilseeds. Biochemical studies by Bafor et al. (1993) indicate that developing seeds of these plants contain an enzyme known as epoxygenase which converts linoleic acid into vernolic acid in a one step reaction. Although many plants including soybeans have enzymes such as lipoxygenase and peroxygenase that can produce epoxy fatty acids in some disease resistance reactions (Blee, 1998), they do not have mechanisms for accumulation of epoxy-triglycerides in their seeds unlike epoxy triglyceride accumulators such as *Stokesia* mentioned above (Bafor et al., 1993; Hildebrand et al., 2001).

The original studies on epoxy fatty acid synthesis and accumulation in oilseeds by Bafor et al. (1993) indicated that the epoxy fatty acid that accumulated in seeds of *E. lagascae*, vernolic acid, is synthesized by an epoxygenase enzyme which is a P450 monooxygenase enzyme. It was assumed that other epoxy fatty acid accumulators such as *Vernonia* similarly synthesized epoxy fatty acids by P450 monooxygenase enzymes.

However studies by Seither (1996), Seither, Avdiushko et al. (1996, 1997) indicated that delta12 fatty acid desaturase-like enzymes are responsible for vernolic acid biosynthesis in epoxy fatty acid accumulators of the Asteraceae such as *Vernonia*, *Crepis* and *Stokesia* unlike the *Euphobiacea* epoxide accumulator, *E. lagascae*, which relied on P450 monooxygenase (Seither, 1996, Seither, Avdiushko et al., 1996, Seither, Avdiushko et al., 1997).

A seed specific P450 monooxygenase family enzyme was cloned from *Euphorbia lagascae*. The international patent application WO02/08269 deals with the description of an enzyme of the cytochrome P450 mono-oxygenase class that is responsible for the epoxide formation. It is encoded by a nucleic acid isolated from *Euphorba lagascae* developing seed cDNA library. This patent application also discloses the nucleotide and amino acid sequence of the cytochrome P450 mono-oxygenase of *Euphorba lagascae*. The fatty acid compositions were monitored, showing accumulation of epoxy fatty acids in transformed plants.

Genes from *Vernonia galamensis* and *Crepis palaestina* have been isolated, and when expressed in plants or yeast, the encoded proteins are capable of converting linoleic acid to vernolic acid (U.S. Pat. No. 5,846,784, WO 98/56922, U.S. Pat. No. 6,329,518 and WO 98/46762).

U.S. Pat. No. 5,846,784 relates to a nucleic acid encoding *Vernonia galamensis* fatty acid modifying enzymes. This nucleic acid is used to transform microbial and soybean embryogenic cells. The expression of this nucleic acid results in production of altered levels of a *Vernonia galamensis* fatty acid modifying enzyme in the transformed cells.

WO 98/56922 international patent application claims the priority of the above cited U.S. patent, it contains further example dealing with the transformation of corn cells and *Arabidopsis* cells. The expression of the *Vernonia* fatty acid epoxidase has been monitored in *Arabidopsis* seeds. The putative vernolic acid represented about 1.5% of the total fatty acids.

U.S. Pat. No. 6,329,518 and international patent application WO98/46762 describe the isolation and characterization of an isolated nucleic acid molecule which encodes a fatty acid epoxygenase from *Crespis palaestina*. They also describe a genetic construct comprising said nucleic acid molecule operatively linked to a promoter sequence that is capable to be transcribed. The protein encoded by this nucleic acid molecule is a delta12 epoxygenase polypeptide which catalyses the epoxygenation of a carbon double bound in linoleic acid to form vernolic acid.

However, the epoxygenase activities from these last plants producing vernolic acid have been shown to be different from the *E. lagascae* enzyme. Unlike the *E. lagascae* enzyme, they are related to the endoplasmic reticulum-localized fatty acid desaturases (WO 94/11516). These fatty acid epoxygenase enzymes are related in sequence to the class of membrane bound enzymes responsible for fatty acid desaturation and fatty acid hydroxylation (Broun and Somerville, 1997). Therefore, there are two distinct classes of genes encoding enzymes capable of vernolic acid epoxide group formation, one that is cytochrome P450-dependant, and the other that is related to the fatty acid desaturases and hydrolases.

The epoxygenase responsible for vernolic acid production in *Stokesia laevis* developing seed is a novel protein.

SUMMARY OF THE INVENTION

The present invention relates to isolated nucleic acid molecules encoding plant enzymes involved in fatty acid modification, these enzymes having sequence homology to membrane bound desaturases. One aspect of the present invention provides an isolated nucleic acid molecule which encodes a delta 12-fatty acid epoxygenase enzyme comprising an amino acid sequence which is at least about 80% homologous to SEQ ID NO.2 or a homologue, an analogue or a derivative thereof which has epoxygenase activity. It is preferred that the isolated nucleic acid molecule encodes an amino acid sequence which is at least 90% identical to SEQ ID NO.2 or a homologue, analogue or derivative thereof.

In a more preferred aspect, the isolated nucleic acid molecule encodes an amino acid sequence which is at least 95% identical to SEQ ID NO.2 or a homologue, analogue or derivative thereof.

The isolated nucleic acid molecule of the invention shall in the most preferred aspect encodes an amino acid sequence which is at least about 98% identical to SEQ ID NO.2 or a homologue, analogue or derivative thereof.

The invention also provides an isolated nucleic acid encoding a delta 12 epoxygenase having the nucleotide sequence of SEQ ID No.1 or its complement. In another embodiment, the invention provides a polypeptide having the sequence of SEQ ID No.2 and having a delta12 epoxygenase activity.

In another embodiment, the invention deals with a chimeric gene comprising the isolated nucleic acid encoding a delta 12 epoxygenase enzyme of the invention operably linked to at least one suitable regulatory sequence that allow the expression of the coding sequence in a host cell. In a preferred aspect, the regulatory sequence of the chimeric gene allow the expression of the coding sequence in a plant cell. In another preferred aspect, the regulatory sequence of the chimeric gene comprises the phaseolin promoter.

In another embodiment, the invention provides a vector comprising the above cited chimeric gene.

In a further aspect, the invention provides an isolated host cell comprising the chimeric gene of the invention or a vector according to the invention. These host cells can be selected from the group comprising fungi, bacteria, insect and plant cells.

In another embodiment, the invention provides a transgenic plant comprising the chimeric gene or the vector of the invention.

A still further aspect of the invention provides a method for producing delta12 epoxy fatty acids which comprises:
 (i) transforming a host cell with the chimeric gene or the vector of the invention;
 (ii) growing the transformed host cells of step (i) under conditions that are suitable for expression of the chimeric gene, wherein the expression of the chimeric gene results in production of altered levels of fatty acid modifying enzyme in the transformed host cell.

In a preferred embodiment, the cell transformed in step (i) of the above cited method is a plant cell.

The invention further provides a method for producing delta12 epoxy fatty acids which comprises the additional step of:
 (iii) regenerating the cell obtained by step (ii) into a plant The invention also provides a method for producing a delta12-epoxygenase enzyme comprising the following steps:
 (i) transforming a microbial or a plant cell with the chimeric gene or with the vector of the invention;
 (ii) growing the transformed cells obtained from step (i) under conditions that results in expression of the delta 12-epoxygenase enzyme. In a preferred embodiment, the disclosed method can be used to produce a *Stokesia laevis* L112-epoxygenase enzyme

BRIEF DESCRIPTION OF THE DRAWINGS

FIGS. 1A-1C show an alignment of the *Stokesia laevis* epoxygenase cDNA with *Veronia* (SEQ ID NO:9) and *Crepis* epoxygenase eDNA (SEQ ID NO:10).

DETAILED DESCRIPTION OF THE INVENTION

The invention relates to isolated nucleic acid molecules homologous to all or a substantial portion of a fatty acid epoxygenase enzyme normally expressed in developing seeds of *Stokesia laevis*. The invention also relates to the construction of a chimeric gene comprising a nucleic acid molecule encoding a polypeptide highly homologous to the epoxygenase enzyme of *Stokesia laevis* operably linked in sense or antisense orientation to suitable regulatory sequences, wherein expression of the chimeric gene results in production of altered levels of the epoxygenase enzyme in a transformed host cell. The invention also relates to a method of production of altered levels of epoxy fatty acid in a host transformed cell or in a transformed organism or tissue.

The term "isolated nucleic acid molecule" refers to a polymer of RNA or DNA that is single- or doubled-stranded, which may optionally include synthetic or modified nucleotides.

The terms "epoxy group", "epoxy fatty acids", "epoxidized fatty acid" or "the product of an epoxygenase" all refer to the introduction of an epoxyide bridge (an oxygen atom covalently bound to carbon atoms that are in turn covalently bond to each other, to form a three member ring that is part of a larger molecular structure) at the site of a double bond in the acyl chain of a fatty acid.

"Delta12-epoxygenase" or "delta 12-epoxidase" refers to an epoxygenase enzyme which catalyses the conversion of the delta 12-carbon bond of a fatty acid substrate to a delta 12 epoxy group.

"Vernolic acid" refers to the fatty acid 12,13-epoxyoctadeca-9-cis-enoic acid which contains eighteen carbon atoms, a cis double bond between the 9 and the 10 carbon atoms, and an epoxy group between the 12 and 13 carbon atoms. The term "delta. 12-epoxy fatty acid" refers to a fatty acid such as vernolic acid that contains an epoxy group between the 12 and 13 carbon atoms.

"Homologue of a nucleotide sequence" is understood according to the invention to mean an isolated nucleic acid molecule which is substantially the same as the nucleic acid molecule of the present invention or its complementary nucleotide sequence, notwithstanding the occurrence within the sequence, of one or more nucleotide substitutions, insertion, deletions or rearrangements. Preferably, a homologue contains no more than about 25 nucleotide changes, preferably from about 1-25, more preferably about 5 to 20 nucleotide changes.

An "analogue" of a nucleotide sequence refers to an isolated nucleic acid molecule which is substantially the same as a nucleic acid molecule of the invention or its complementary nucleotide sequence, notwithstanding the occurrence of any non-nucleotide constituents not normally present in said isolated nucleic acid molecule. An analogue encodes a polypeptide having the same activity or function of a polypeptide of the invention.

The term "derivative" of a nucleotide sequence refers to any isolated nucleic acid molecule which contains significant sequence similarity to another sequence or a part thereof. Preferably a derivative exhibits about 50 to about 98% sequence similarity to the specified nucleotide sequence, more preferably about 70 to about 95% sequence similarity, and most preferably about 80%, 90%, 95% or 98% sequence similarity.

The term "gene" refers to a nucleic acid molecule that expresses a specific protein, including regulatory 5' non-coding sequences and 3' non coding. "Chimeric gene" refers to a gene that does not exist in nature, comprising the following elements in 5' to 3' orientation: a promoter functional in a host (preferably a plant) cell, as defined above, a polynucleotide of the invention and a terminator functional in said cell. Other elements, for example an enhancer(s), may also be present. These chimeric genes may be incorporated into vectors, as defined above.

"Coding sequence" refers to a nucleotide sequence that codes for a specific amino acid sequence.

"Regulatory sequences" refers to nucleotide sequences located upstream (5' non-coding sequences), within or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. The coding sequence is located 3' to the promoter sequence. The promoter consists of proximal and more distal upstream elements, the latter elements are often referred as enhancers.

"Operably linked" refers to the association of nucleic acid sequences on a single nucleic acid fragment so that the function of one is affected by the other. A promoter that is operably linked with a coding sequence is capable of affecting the expression of that coding sequence. Coding sequences can be operably linked to regulatory sequences in sense or antisense orientation.

"Plant cell" is understood according to the invention to mean any cell derived from a monocotyledonous or a dicotyledonous plant and capable of constituting undifferentiated tissues such as calli, differentiated tissues such as embryos, portions of monocotyledonous plants, monocotyledonous plants or seeds. "Plant" is understood to mean any differentiated multicellular organism capable of photosynthesis, more particularly monocotyledonous or dicotyledonous plants.

As regulatory terminator sequence or polyadenylation sequence, there may be used any corresponding sequence of bacterial origin, such as for example the nos terminator from *Agrobacterium tumefaciens* of plant origin, such as for example a histone terminator as described in European application EP 633 317.

Standard recombinant DNA and molecular cloning techniques used herein are well known in the art and are described more fully in Sambrook, J., Fritsch, E. F. and Maniatis T. Molecular Cloning: A Laboratory Manual; Cold Spring Harbor Laboratory Press: Cold Spring Harbor, 1989), incorporated herein by reference.

This invention relates to isolated plant polynucleotides encoding plant fatty acid modifying enzymes. The nucleotide sequence encoding *Stokesia laevis* epoxygenase enzyme is provided in SEQ ID No.1; and the deduced amino acid sequence is provided in SEQ ID No.2. Fatty acid epoxygenase enzyme genes from other plants can now be identified by comparison of random DNA sequences to the *Stokesia laevis* sequences provided herein.

Plants are known to accumulate a wide diversity of unusual fatty acids, some of which have industrial use. Epoxy fatty acids, such as vernolic acid, are an example of a an uncommon fatty acid that accumulates in triacylglycerol of a few plant species that is valuable for various industrial uses including as plasticizers. *Stokesia laevis* seed oil is made up of about 60-70% vernolic acid (12,13-epoxy-9-octadecenoic acid). cDNAs encoding epoxygenases from *Crepis palaestina* (Lee. et al., 1998) and *Vernonia galamensis* (Hitz, 1998) have been cloned and found to be members of a growing family of delta12 fatty acid desaturase-like analogs that also includes hydroxylases, acetylenases and conjugases.

Degenerate primers were designed on the basis of conserved sequences of these delta12 desaturase-like genes, and an apparent full-length epoxygenase gene from *S. laevis* was isolated using RT-PCR and RACE strategies. The cDNA is 1.4 kb (SEQ ID NO. 1), the ORF 1134 bp and it encodes 378 amino acids. The similarities of this gene with epoxygenase of *Vernonia* and *Crepis*, delta 12 desaturase of soybean, FAD 2-1 and FAD 2-2 are 84.3%, 69.4%. 50.4% and 56.2%, respectively.

The amino acid sequence encoded by the cDNA clone disclosed in SEQ ID No.1 has been compared to the those amino acid sequences listed in GenBank using the BLAST program with standard parameters (Altschul et al., 1990). The sequence of the (8,11) linoleoyl desaturase of *Calendula officinalis* shows the highest homology percentage (80%) with SEQ ID No.2. The *Crepis palaestina* delta12-epoxygenase presents a homology of 78% with the sequence of the invention. It does not show any other signification homology with epoxygenase enzymes of other origin.

The nucleic acid molecules of the instant invention and fragments thereof may be used to isolate cDNAs and genes encoding homologous fatty acids modifying enzymes from the same or other species. Examples of sequence-dependent protocols include but are not limited to, methods of nucleic acid hybridization, methods of DNA and RNA amplification.

The nucleic acid molecules of the instant invention may be used to create transgenic plants in which the *Stokesia laevis* modifying enzyme is present at a higher level than normal or in cell types or developmental stages in which it is not normally found. The over expression of the *Stokesia laevis* epoxygenase enzyme may be useful for causing the biosynthesis and accumulation of epoxy fatty acids in those cells. It is particularly useful to over produce this epoxy fatty acids in the cells of the seeds of oilseed crop plants.

Over expression of the *Stokesia laevis* delta 12-epoxygenase enzyme may be accomplished by cloning the gene under the control of a strong promoter capable of directing the expression in the desired tissues at the desired stage of development.

The present invention also relates to a cloning or expression vector for the transformation of a cell, and preferably a plant cell. The vector according to the invention comprises, in addition to the above chimeric gene, at least one origin of replication. This vector may consist of a plasmid, a cosmid, a bacteriophage or a virus, transformed by the introduction of the chimeric gene according to the invention. Such vectors for transforming cells are well known to persons skilled in the art and are widely described in the literature. Preferably, the vector for transforming plant cells or plants according to the invention is a plasmid.

The invention also provides a method of transforming plant cells by integration of at least one nucleic acid molecule or one chimeric gene as defined above, which transformation may be obtained by any known in the art consists in bombarding cells or protoplasts with particles to which DNA sequences are attached. Another art known method consists in using, as means of transferring into the plant, a chimeric gene inserted into an *Agrobacterium rhizogenes* Ri or *Agrobacterium tumefaciens* Ti plasmid. Other methods may be used, such as microinjection or electroporation, or direct precipitation by means of PEG. Persons skilled in the art can readily choose the appropriate method according to the nature of the cell or of the plant.

The present invention also provides transformed plant cells or plants producing epoxy fatty acids and containing at least one chimeric gene according to the invention defined above. The subject of the invention also includes the plants containing transformed cells, in particular the plants regenerated from the transformed cells. The regeneration is obtained by any appropriate method which depends on the nature of the species. For the methods of transforming plant cells and of regenerating plants, there may be mentioned in particular the following patents and patent applications: U.S. Pat. Nos. 4,459,355, 4,536,475, 5,464,763, 5,177,010, 5,187,073, EP 267 159, EP 604 662, EP 672 752, U.S. Pat. Nos. 4,945,050, 5,036,006, 5,100,792, 5,371,014, 5,478,744, 5,179,022, 5,565,346, 5,484,956, 5,508,468, 5,538,877, 5,554,798, 5,489,520, 5,510,318, 5,204,253, 5,405,765, EP 442 174, EP 486 233, EP 486234, EP 539 563, EP 674 725, WO 91/02071 and WO 95/06128., the relevant portions of which are incorporated by reference.

The constructs of the invention can be used to generate transgenic plants in any type of plant, i.e., monocots or dicots. The skilled practitioner, using methods known in the art, can readily transform any plant type using the isolated DNA molecules and vectors of the invention. For example, a transgenic plant of the invention can be produced using *Agrobacterium tumefaciens* mediated DNA transfer, preferably with a disarmed T-DNA vector, electroporation, direct DNA transfer, and particle bombardment. Techniques are well known in the art for introducing nucleic acids into monocots as well as dicots, as are the techniques for culturing such plants and plant tissues and regenerating them.

The constructs of the present invention can be used to generate transgenic plants, seeds or protoplasts, and may be used in any plant tissue, e.g., roots, stems, leaves, flowers, stems, pollen, or seeds.

For some applications it may be useful to direct the instant *Stokesia laevis* delta 12-epoxygenase enzyme to different cellular compartments, or facilitate its secretion from the cell. If desired appropriate intracellular targeting sequences or signal sequences can be operrably linked to the chimeric sequences.

The present invention also relates to the transformed plants derived from cultivating and/or crossing the above regenerated plants, as well as the transformed plant seeds.

The following non-limiting examples illustrate the invention.

EXAMPLE 1 cDNA Cloning

A partial *Stokesia laevis* epoxygenase cDNA fragment was obtained using a RT-PCR kit (Promega) using RNA from developing seeds as a template. The PCR mixtures contained ~1 g of total RNA template, 0.2 mM dNTPs, 2.5 U of AMV reverse transcriptase, 2.5 U of Tfl polymase and ~1 M each of two degenerate primers described below. Reaction mixtures were incubated in a thermocycler (Perkin Elmer, Model 2400) for 45 minutes at 48 degrees C., followed by 2 minutes at 94 degrees C. and 40 cycles of 30 seconds at 94 degrees C., 30 seconds at 500 C. and 1 minute at 72 degrees C. The PCR primers used were a 5' epoxy and 3' epoxy which represent two peptides sequences, CHECGHHA-SEQ ID NO.3 and HDVTHTHV-SEQ ID NO.4, which peptide sequences are the conserved regions in amino acid sequences of desaturase-like epoxygenases of *Crepis palaestina* and *Vernonia galamensis* and delta 12, extracted from the gel using Gel Extraction kit (Qiagen) and subcloned into the pGEM-T Easy vector (Promega). The DNA inserted had both strands sequenced.

For determination of the full-length cDNA sequence, a RACE (Rapid Amplification of cDNA Ends) strategy was applied. A cDNA was synthesized from poly (A) +RNA of developing seeds of *S. laevis* using a Marathon cDNA Amplification Kit (Clontech). Two primers from the sequence information of the partial cDNA fragment of *S. laevis* epoxygenase were designed; 5' ST(CGCAACCTG-GATTCGCTCACGCTCGG-SEQ ID No.5, and 3' ST(CCCAGCTCAGGACTTACTCCACATACG-SEQ ID No.6. The 5'-half and 3'-half of the cDNAs were amplified using the PCR conditions described in the user manual of the kit.

Fractionation of the amplified fragments, cloning and sequencing were carried out as described above.

The cDNA sequence (SEQ ID No.1) was determined to be 1134 bp. It was not chimeric and did not contain any errors, which was proven by separate two PCRs with the most distal primer pairs and direct DNA sequencing on those PCR products.

The ATG start site of the open reading frame for 378 amino acids (SEQ ID NO:2) is at 93 and the stop codon is at 1227.

EXAMPLE 2

Cloning of *Stokesia* epoxygenase cDNA for Expression in *Arabidopsis thaliana*

The epoxygenase cDNA of *Stokesia* was expressed in *Arabidopsis thaliana*. A BsmBl site was introduced at the first ATG and a Sinai site was introduced at the end of the ORF (Qpen reading frame or coding sequence) of the cDNA by PCR mutagenesis. The ORF sequence of the cDNA was amplified using two primers: StexpF (GACGCGTCTTC-CCATGTCGGATTCATATGATG-SEQ ID NO. 7and StexpR (GACGCCCGGGVrACATTTTATGGTACCAAT-ATGTCCC-SEQ ID NO.8, BmsBl and SmaI sites are underlined), and cloned into the pGEM-T Easy vector and verified by DNA sequencing. The BsmBl-SmaI fragment covering the entire open reading frame of the cDNA was cut out from pGEM-T Easy vector and ultimately cloned into the respective site of pPHI4752 vector, which contains a phaseolin promoter cassette. The PstI fragment including the cDNA with the phaseolin cassette was cut out from the pPHI 4752 vector and cloned into the respective multi-cloning site of pcambiaCAMBIA 1201, T-DNA vector.

This construct, pCAMBIA-ST was transformed into Agrobacterium tumefaciens, strain C58 harboring GV3850 vector by a triparental matings method. The original pCAMBIA 1201 was also transformed into 8 Agrobacterium

EXAMPLE 3

Transformation of Arabidopsis thaliana Plants as a Control.
Arabidopsis thaliana ecotype Columbia plants were transformed with the Agrobacterium carrying pCAMBIA-ST or pCAMBIA 1201 using a simplified dipping method (Clough and Bent 1998). T1 seeds were collected and cultured on selection media (MS salts, B5 vitamins, 1% sucrose, 25 mg/L hygromycin, 500 mg/L cefotaxime and 0.8% Phytagar, pH 5.8). Surviving plantlets were transferred into soil and T 2 seeds were collected.

EXAMPLE 4

Lipid extraction: For lipid extraction, seeds were ground in chloroform-methanol (2:1). The extracts were brought to dryness under a $N_2$ gas stream. The lipid residues were immediately dissolved in a few drops of diazomethane and 0.5 mL sodium methoxide solution and shaken for 45 minutes at room temperature. The methyl ester fatty acids were extracted in the hexane-upper layer (1 mL). The samples were analyzed using gas chromatography-mass spectrometry or gas chromatography by injecting 1 microliter or 5 microliters of hexane extract, respectively.

Figure 1C:
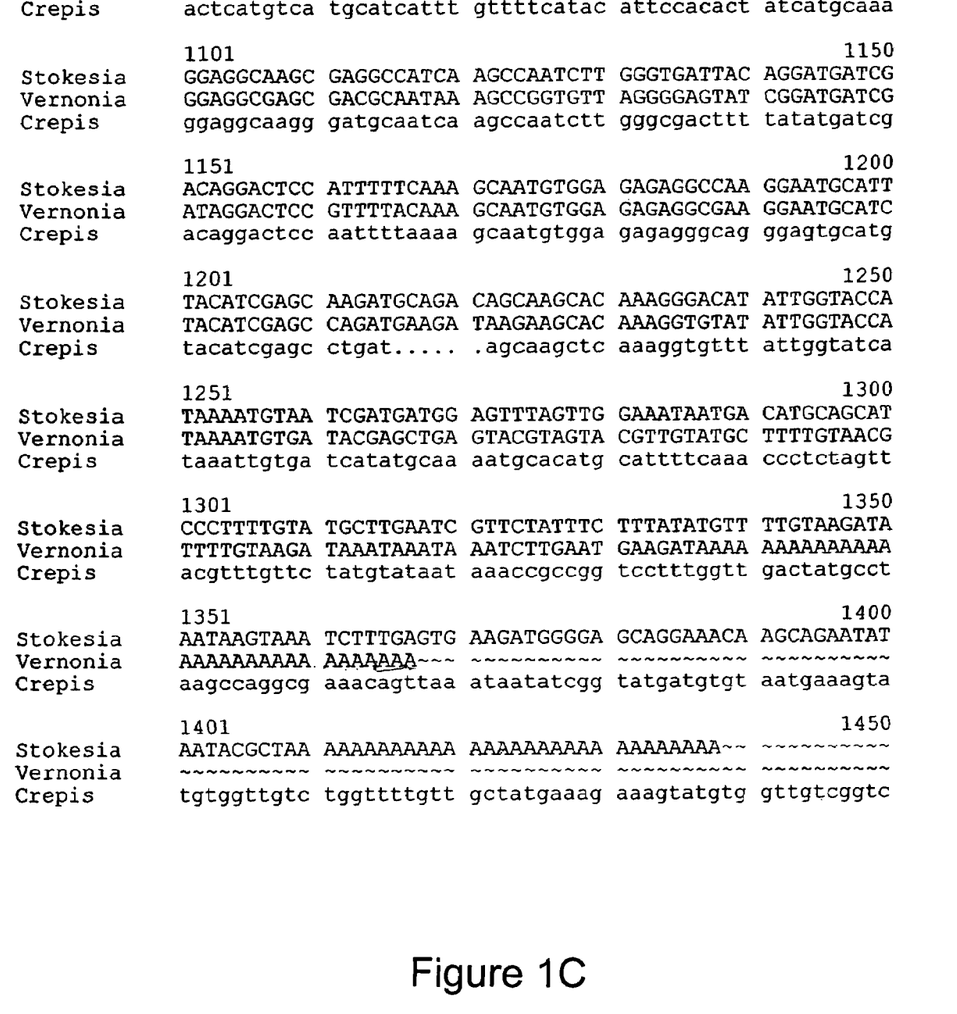
Figure 2A:
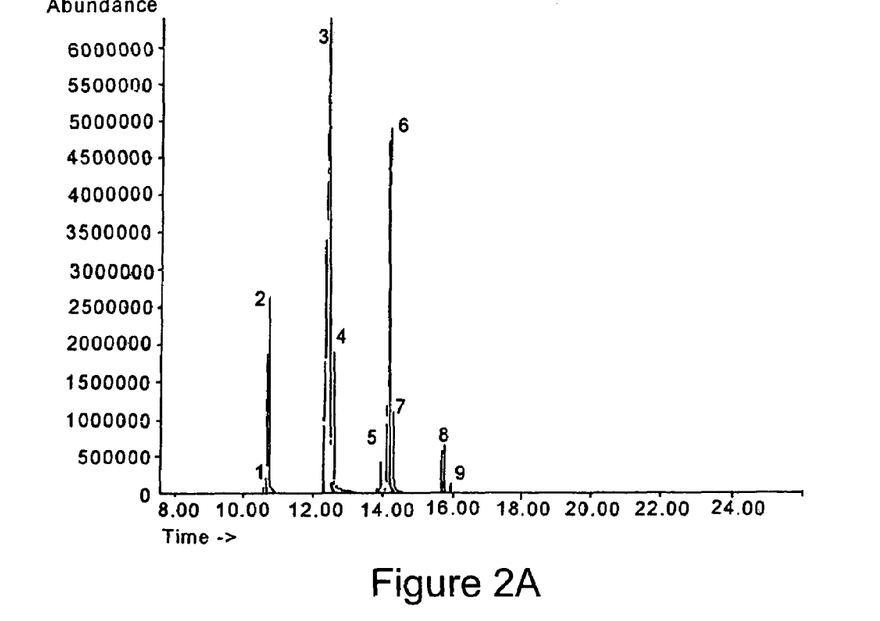
FIGS. 2A-2D: GC-MS analysis of fatty acid derivatives from transgenic *Arabidopsis* seeds. (A) Chromatograms from transgenic *Arabidopsis* transformed with pCAMBIA 1202 comprising the cDNA from *Stokesia laevis*. (B) Chromatograms from *Arabidopsis* seeds transformed with empty vector, pCAMBIA 1201 as a control. (C) Mass spectrum of the compound giving rise to peak 5 at 13.94 min. in chromatogram (A), and (D) a standard vernolic acid. M/z, mass-to-charge ratio.
Figure 2B:
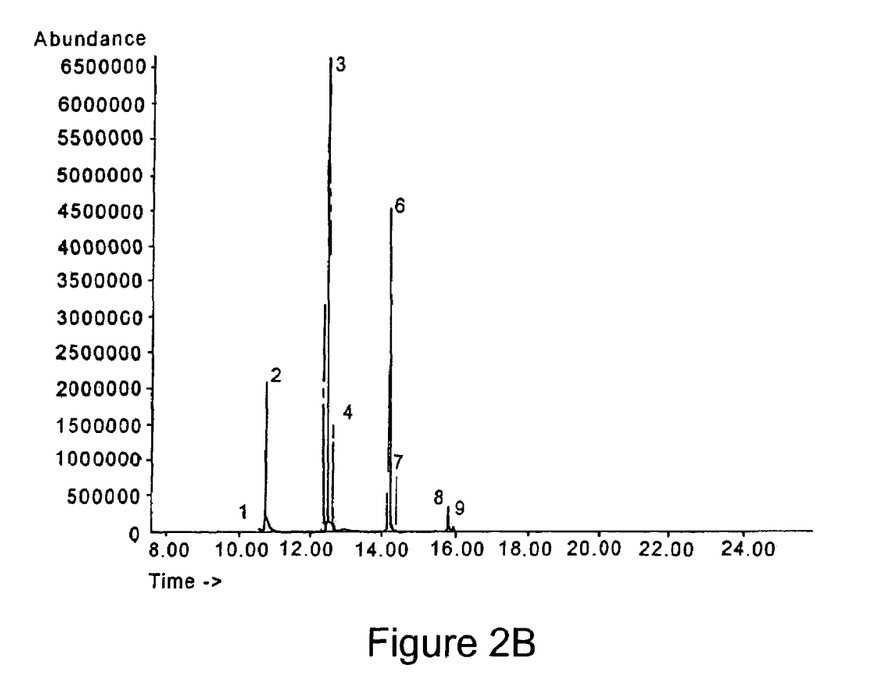
Figure 2C:
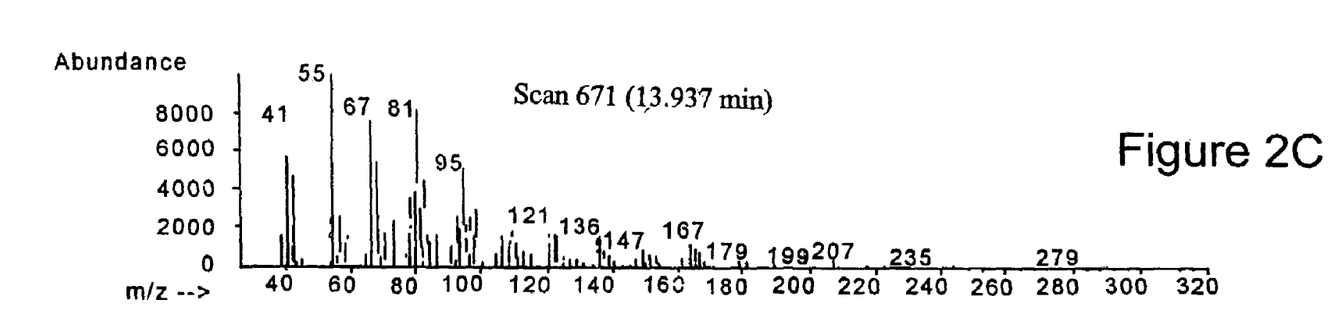
Figure 2D:
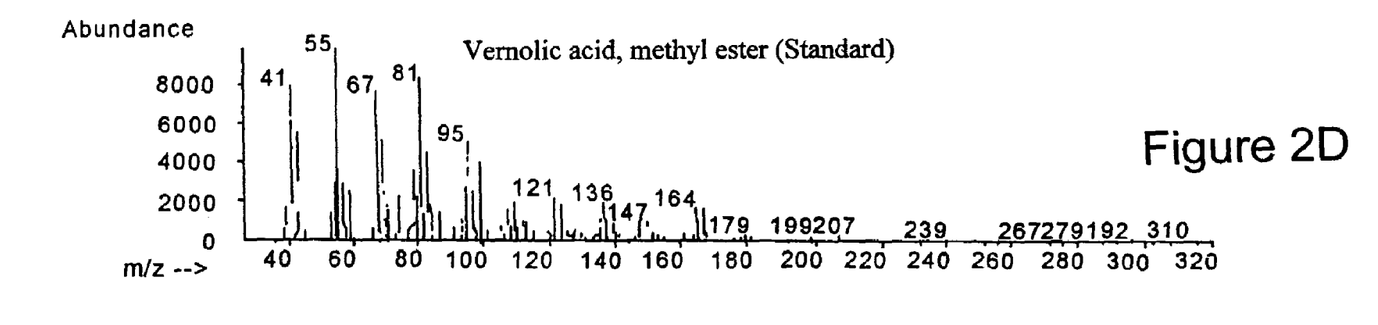

To verify the enzymatic activity of the gene product, the protein was expressed in seeds of A. Thaliana plants. In seeds of transgenic Arabidopsis, vernolic acid was detected with GC-MS, but no vernolic acid was detected in control plants transformed with the empty vector (FIGS. 1A-1C).

Table 1: Seed oil fatty acid composition for transgenic Arabidopsis thaliana carrying the Stokesia laevis epoxygenase. Control seeds of vector transformed T2 Arabidopsis seeds=the average of 2 replications. Plants 1 to 16 are T2 s d analyses of different epoxygenas transgenic plants. *Va=vernolic acid.

TABLE 1

| plant | 16:0 | 16:1 | 18:0 | 18:1 | 18:2 | 18:3 | 20:0 | 20:1 | 22:0 | 22:1 | Va* | Total |
|---|---|---|---|---|---|---|---|---|---|---|---|---|
| Seed Fatty Acid Contents (µg/mg D.W.) | | | | | | | | | | | | |
| 1 | 10.6 | 0.6 | 3.6 | 33.8 | 23.8 | 19.4 | 1.6 | 16.0 | 0.7 | 0.9 | 1.3 | 112.2 |
| 2 | 9.6 | 1.1 | 4.6 | 69.1 | 20.2 | 19.4 | 2.2 | 32.2 | 0.7 | 1.5 | 5.1 | 165.6 |
| 3 | 30.6 | 2.7 | 14.9 | 141.5 | 38.0 | 36.6 | 6.8 | 64.2 | ND | 3.3 | 10.6 | 349.1 |
| 4 | 18.1 | 1.2 | 7.8 | 97.9 | 26.7 | 25.3 | 3.7 | 40.7 | 0.8 | 1.7 | 5.5 | 229.5 |
| 5 | 15.7 | 1.0 | 6.9 | 65.7 | 34.6 | 28.2 | 3.5 | 36.4 | 1.0 | 2.0 | 2.9 | 197.9 |
| 6 | 30.6 | 2.7 | 14.7 | 151.3 | 56.3 | 50.8 | 6.8 | 78.1 | 1.7 | 3.6 | 9.4 | 405.9 |
| 7 | 20.4 | 1.9 | 7.7 | 83.1 | 28.0 | 27.7 | 2.7 | 33.6 | 0.7 | 1.2 | 5.3 | 212.3 |
| 8 | 17.8 | 1.5 | 7.8 | 108.9 | 35.7 | 32.8 | 3.4 | 47.5 | 1.0 | 1.9 | 5.0 | 263.5 |
| 9 | 18.1 | 1.6 | 8.4 | 113.3 | 21.8 | 25.6 | 3.2 | 47.5 | 1.6 | 1.6 | 7.0 | 249.8 |
| 10 | 23.6 | 2.2 | 10.9 | 140.5 | 46.0 | 39.8 | 4.5 | 59.5 | 1.2 | 2.4 | 7.0 | 337.6 |
| 11 | 17.9 | 1.4 | 8.0 | 80.3 | 46.6 | 38.3 | 3.9 | 45.3 | 1.4 | 2.2 | 3.7 | 248.9 |
| 12 | 15.3 | 1.4 | 7.5 | 113.5 | 21.4 | 19.6 | 3.2 | 49.6 | ND | 1.9 | 6.2 | 239.6 |
| 13 | 15.8 | 1.2 | 7.3 | 79.7 | 25.3 | 27.0 | 3.4 | 38.3 | 0.9 | 1.7 | 6.4 | 207.0 |
| 14 | 21.1 | 1.6 | 9.0 | 106.6 | 34.2 | 31.4 | 3.8 | 48.7 | 1.0 | 1.9 | 7.0 | 266.1 |
| 15 | 15.0 | 1.4 | 7.0 | 72.6 | 26.2 | 21.5 | 3.3 | 36.7 | 0.9 | 1.8 | 4.9 | 169.0 |
| 16 | 17.4 | 1.5 | 7.2 | 59.8 | 28.0 | 28.7 | 3.4 | 31.3 | 1.0 | 1.6 | 5.8 | 185.8 |
| Average | 18.8 | 1.6 | 8.3 | 94.9 | 32.1 | 29.5 | 3.7 | 44.1 | 0.9 | 1.9 | 5.8 | 241.2 |
| Ave. CTRL | 23.5 | 1.8 | 8.3 | 76.3 | 60.9 | 40.0 | 3.4 | 33.9 | 1.3 | 1.5 | 0.0 | 253.8 |
| Seed Fatty Acid Composition (% of Total Fatty Acids) | | | | | | | | | | | | |
| 1 | 9.5 | 0.6 | 3.2 | 30.1 | 21.2 | 17.3 | 1.4 | 14.3 | 0.6 | 0.8 | 1.1 | |
| 2 | 5.8 | 0.7 | 2.8 | 41.7 | 12.2 | 11.7 | 1.3 | 19.4 | 0.4 | 0.9 | 3.1 | |
| 3 | 8.8 | 0.8 | 4.3 | 40.5 | 10.9 | 10.5 | 2.0 | 18.4 | 0.0 | 1.0 | 3.0 | |
| 4 | 7.9 | 0.5 | 3.4 | 42.7 | 11.6 | 11.0 | 1.6 | 17.7 | 0.3 | 0.8 | 2.4 | |
| 5 | 7.9 | 0.5 | 3.5 | 33.2 | 17.5 | 14.2 | 1.8 | 18.4 | 0.5 | 1.0 | 1.4 | |
| 6 | 7.5 | 0.7 | 3.6 | 37.3 | 13.9 | 12.5 | 1.7 | 19.2 | 0.4 | 0.9 | 2.3 | |
| 7 | 9.6 | 0.9 | 3.6 | 39.1 | 13.2 | 13.0 | 1.3 | 15.8 | 0.3 | 0.6 | 2.5 | |
| 8 | 6.8 | 0.6 | 3.0 | 41.4 | 13.6 | 12.5 | 1.3 | 18.0 | 0.4 | 0.7 | 1.9 | |
| 9 | 7.3 | 0.7 | 3.4 | 45.4 | 8.7 | 10.3 | 1.3 | 19.0 | 0.6 | 0.6 | 2.8 | |
| 10 | 7.0 | 0.7 | 3.2 | 41.6 | 13.6 | 11.8 | 1.3 | 17.6 | 0.4 | 0.7 | 2.1 | |
| 11 | 7.2 | 0.6 | 3.2 | 32.3 | 18.7 | 15.4 | 1.6 | 18.2 | 0.5 | 0.9 | 1.5 | |
| 12 | 6.4 | 0.6 | 3.1 | 47.4 | 8.9 | 8.2 | 1.4 | 20.7 | 0.0 | 0.8 | 2.6 | |
| 13 | 7.6 | 0.6 | 3.5 | 38.5 | 12.2 | 13.0 | 1.7 | 18.5 | 0.4 | 0.8 | 3.1 | |
| 14 | 7.9 | 0.6 | 3.4 | 40.0 | 12.8 | 11.8 | 1.4 | 18.3 | 0.4 | 0.7 | 2.6 | |
| 15 | 8.0 | 0.7 | 3.7 | 38.4 | 13.9 | 11.4 | 1.8 | 19.4 | 0.5 | 1.0 | 2.6 | |
| 16 | 9.4 | 0.8 | 3.9 | 32.2 | 15.1 | 15.5 | 1.8 | 16.9 | 0.5 | 0.9 | 3.1 | |
| Average | 7.8 | 0.6 | 3.4 | 38.9 | 13.6 | 12.5 | 1.5 | 18.1 | 0.4 | 0.8 | 2.4 | |
| Ave. CTRL | 9.4 | 0.7 | 3.3 | 31.0 | 24.3 | 15.9 | 1.3 | 13.5 | 0.5 | 0.6 | 0.0 | |

EXAMPLE 5

Stokesia epoxygenase Expression in Soybeans

Figure 3A:
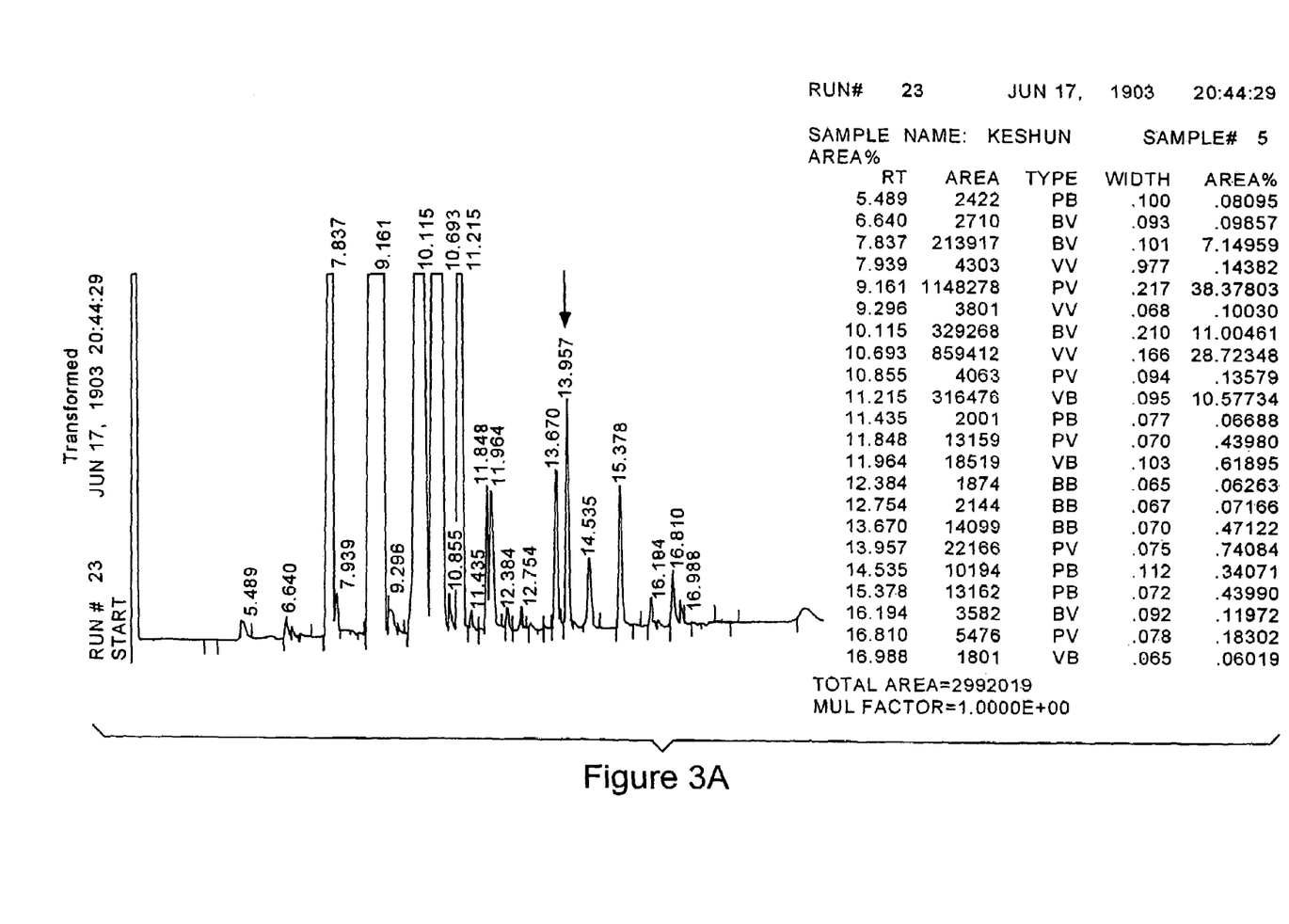
FIGS. 3A-3B show (A) elution of Vernolic acid from a column at 13.957 min. and (B) a control.
Figure 3B:
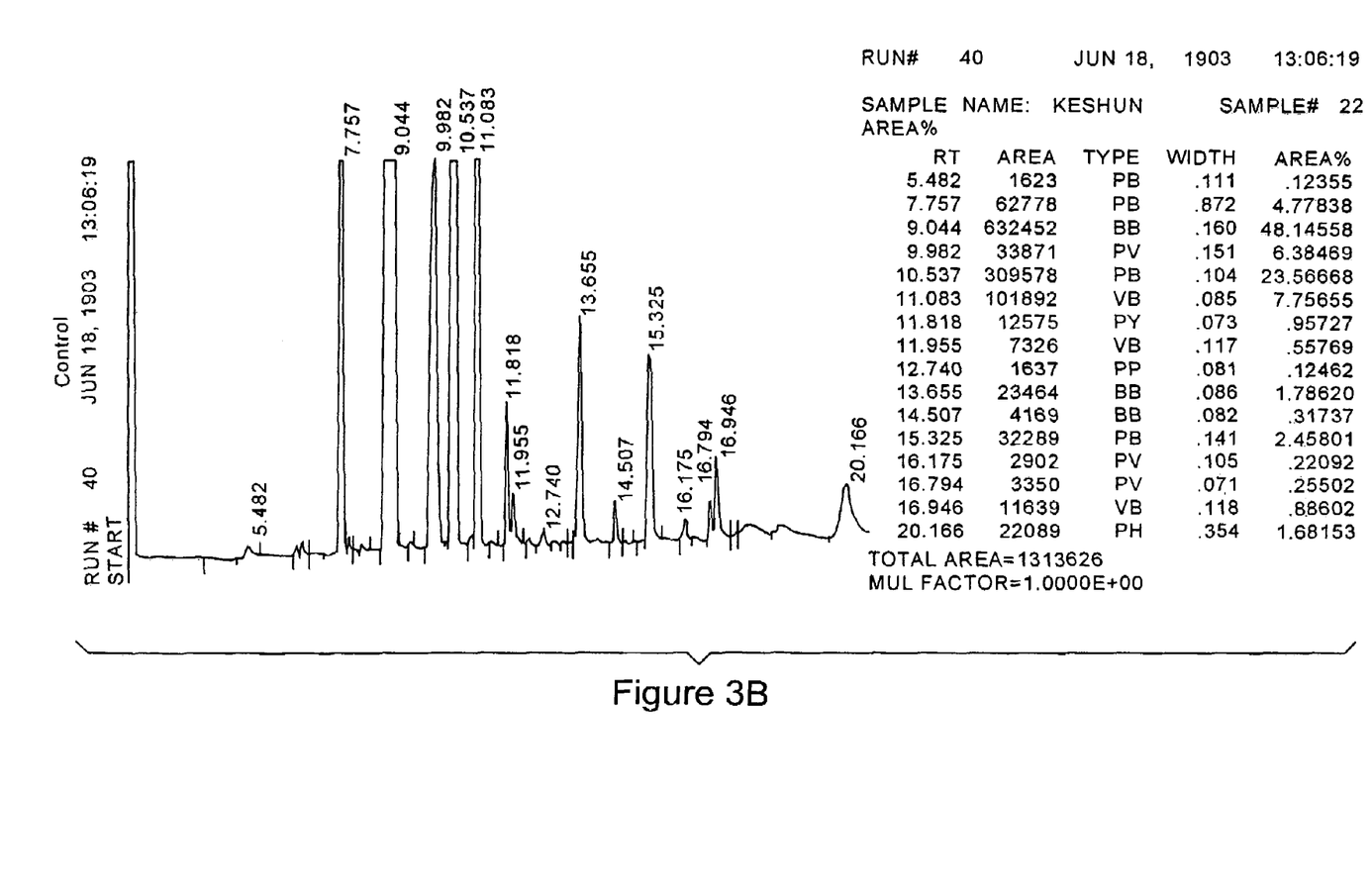

A soybean line expressing the *Stokesia* epoxygenase gene was generated using the methods described above. The transferred soybean clearly shows elevated vernolic acid relative to control soybean somatic embryos. FIGS. 3A-2B. Vernolic acid elutes from the column at 13.957 min. as designated by the arrow in FIGS. 3A.

As shown in Table 2, the vernolic acid accumulation in the soy bean transgenic line 4128 was low, but>10 fold more than the control (Table 2).

TABLE 2

Production of matured soybean somatic embryos from Line 4128 expressing *Stokesia laevis* epoxygenase

| Somatic embryos | Vernolic acid (% of total fatty acids) |
|---|---|
| Control | <0.09 |
| *Stokesia laevis* epoxygenase | 0.92 ± 0.20 |

Data are means ± STD (n = 6)

EXAMPLE 6

Isolation of an Analogue, Homolog or Derivative of *Stokesia laevis* Delta 12-Epoxygenase Gene Sequence similarity to the *Stokesia laevis* delta 12-epoxygenase gene is used to isolate analogues, homologs and derivatives of the delta 12-epoxygenase gene. Using probes that are specific for the *Stokesia laevis* delta 12-epoxygenase gene and high stringency hybridization and wash conditions, e.g., an example of highly stringent wash conditions is 0.15 M NaCl at 72° C. for about 15 minutes; an example of stringent wash conditions is a 0.2×SSC wash at 65° C. for 15 minutes (See, Sambrook et al. (1989) Molecular Cloning—A Laboratory Manual (2nd ed.) Vol. 1-3, Cold Spring Harbor Laboratory, Cold Spring Harbor Press, N.Y., for a description of SSC buffer and description of stringency conditions for nucleic acid hybridization), polynucleotide sequences that are analogues, homologs or derivatives of the delta 12-epoxygenase are isolated. In general, a signal to noise ratio of 2× (or higher) than that observed for an unrelated probe in the particular hybridization assay indicates detection of a specific hybridization.

The invention claimed is:

1. An isolated nucleic acid molecule comprising a nucleotide sequence selected from the group consisting of: (a) the nucleotide sequence of SEQ ID NO: 1; (b) the nucleotide sequence which is the full-length complement of (a); and (c) a nucleotide sequence which hybridizes under high stringency conditions to the complement of SEQ ID NO: 1, wherein said high stringency conditions comprise a wash in 0.2×SSC at 65° C. for 15 minutes, and wherein said nucleotide sequence encodes a protein having delta 12-fatty acid epoxygenase activity.

2. A chimeric DNA construct comprising the isolated nucleic acid molecule of claim 1 operably linked to at least one regulatory sequence that allows the expression of the nucleic acid molecule in a host cell.

3. The chimeric DNA construct according to claim wherein the at least one regulatory sequence allows expression of the nucleic acid molecule in a bacterial, fungal, insect or plant seed cell.

4. The chimeric DNA construct according to claim 2 wherein the at least one regulatory sequence is a phaseolin promoter.

5. A vector comprising the chimeric DNA construct according to claim 2.

6. A transformed host cell comprising an isolated nucleic acid molecule comprising a nucleotide sequence selected from the group consisting of: (a) the nucleotide sequence of SEQ ID NO: 1; (b) the nucleotide sequence which is the full-length complement of (a); and (c) a nucleotide sequence which hybridizes under high stringency conditions to the complement of SEQ ID NO: 1, wherein said high stringency conditions comprise a wash in 0.2×SSC at 65° C. for 15 minutes, and wherein said nucleotide sequence encodes a protein having delta 12-fatty acid epoxygenase activity.

7. An isolated host cell comprising a vector which comprises an isolated nucleic acid molecule having a nucleotide sequence selected from the group consisting of: (a) the nucleotide sequence of SEQ ID NO: 1; (b) the nucleotide sequence which is the full-length complement of (a); and (c) a nucleotide sequence which hybridizes under high stringency conditions to the complement of SEQ ID NO: 1, wherein said high stringency conditions comprise a wash in 0.2×SSC at 65° C. for 15 minutes, and wherein said nucleotide sequence encodes a protein having delta 12-fatty acid epoxygenase activity, and wherein the nucleotide sequence is operably linked to at least one regulatory sequence that allows the expression of the nucleotide sequence in the host cell.

8. The host cell of claim 7 wherein the host cell is selected from the group consisting of yeast, bacterium, insect and plant seed cell.

9. A transgenic plant seed cell comprising an isolated nucleic acid molecule comprising a nucleotide sequence selected from the group consisting of: (a) the nucleotide sequence of SEQ ID NO: 1; (b) the nucleotide sequence which is the full-length complement of (a); and (c) a nucleotide sequence which hybridizes under high stringency conditions to the complement of SEQ ID NO: 1, wherein said high stringency conditions comprise a wash in 0.2×SSC at 65° C. for 15 minutes, and wherein said nucleotide sequence encodes a protein having delta 12-fatty acid epoxygenase activity.

10. A transgenic plant seed cell comprising a vector which comprises an isolated nucleic acid molecule having a nucleotide sequence selected from the group consisting of: (a) the nucleotide sequence of SEQ ID NO: 1; (b) the nucleotide sequence which is the full-length complement of (a); and (c) a nucleotide sequence which hybridizes under high stringency conditions to the complement of SEQ ID NO: 1, wherein said high stringency conditions comprise a wash in 0.2×SSC at 65° C. for 15 minutes, and wherein said nucleotide sequence encodes a protein having delta 12-fatty acid epoxygenase activity, and wherein the nucleotide sequence is operably linked to at least one regulatory sequence that allows the expression of the nucleotide sequence in the plant seed cell.

* * * * *